US012758725B2

(12) United States Patent
Hepting

(10) Patent No.: US 12,758,725 B2
(45) Date of Patent: Oct. 13, 2026

(54) VENTILATION DEVICE COMPRISING AN INPUT/OUTPUT DEVICE SECURED TO AN INNER FUNCTIONAL ASSEMBLY

(71) Applicant: Hamilton Medical AG, Bonaduz (CH)

(72) Inventor: Daniel Hepting, Maladers (CH)

(73) Assignee: Hamilton Medical AG, Bonaduz (CH)

(*) Notice: Subject to any disclaimer, the term of this patent is extended or adjusted under 35 U.S.C. 154(b) by 753 days.

(21) Appl. No.: 18/021,139

(22) PCT Filed: Aug. 26, 2021

(86) PCT No.: PCT/EP2021/073687

§ 371 (c)(1),
(2) Date: Feb. 13, 2023

(87) PCT Pub. No.: WO2022/043472

PCT Pub. Date: Mar. 3, 2022

(65) Prior Publication Data

US 2023/0310769 A1 Oct. 5, 2023

(30) Foreign Application Priority Data

Aug. 31, 2020 (DE) ..................... 10 2020 122 672.1

(51) Int. Cl.
*A61M 16/00* (2006.01)

(52) U.S. Cl.
CPC . *A61M 16/0003* (2014.02); *A61M 2016/0027* (2013.01); *A61M 2202/0208* (2013.01); *A61M 2205/505* (2013.01); *A61M 2207/00* (2013.01)

(58) Field of Classification Search
None
See application file for complete search history.

(56) References Cited

U.S. PATENT DOCUMENTS

| | | | | |
|---|---|---|---|---|
| 6,335,806 B1 * | 1/2002 | Chiang | .................... | H04N 1/10 382/312 |
| 2003/0172931 A1 * | 9/2003 | Kerechanin, II | ...... | A61M 16/00 128/204.21 |
| 2005/0051168 A1 | 3/2005 | Devries et al. | | |
| 2007/0169776 A1 * | 7/2007 | Kepler | ..................... | C07K 7/56 128/200.14 |

(Continued)

OTHER PUBLICATIONS

German Search Report for corresponding DE 10 2020 122 672.1 mailed May 20, 2021, 8 pgs.

(Continued)

*Primary Examiner* — Timothy A Stanis
*Assistant Examiner* — Thomas Z Chang
(74) *Attorney, Agent, or Firm* — Rankin Hill & Clark LLP

(57) ABSTRACT

A ventilation device for an at least supportive artificial ventilation of patients including a device housing, a functional assembly, which is received in the device housing in an operational position and which has at least one controller as a functional unit, and an input/output device which is arranged on the device housing in an assembly position, the input/output device is connected to the controller through an opening in the device housing so as to transmit signals, and the input/output device is secured directly to the functional assembly so as to prevent removal of the input/output device from its assembly position away from the device housing in a lifting direction.

14 Claims, 5 Drawing Sheets

(56) References Cited

U.S. PATENT DOCUMENTS

| | | | | |
|---|---|---|---|---|
| 2014/0352695 | A1 | 12/2014 | Friberg et al. | |
| 2015/0273167 | A1* | 10/2015 | Feldhahn | A61M 16/021 128/204.21 |
| 2016/0158478 | A1* | 6/2016 | Bertinetti | A61M 16/0816 128/202.22 |
| 2016/0354557 | A1* | 12/2016 | McPherson Allnutt | A61M 16/06 |
| 2019/0217042 | A1* | 7/2019 | Zapol | A61M 16/04 |
| 2020/0129721 | A1 | 4/2020 | Tappehorn et al. | |
| 2021/0187223 | A1* | 6/2021 | Sing | A61M 16/0683 |
| 2022/0023650 | A1* | 1/2022 | Perl | A61M 16/1005 |
| 2023/0158266 | A1* | 5/2023 | Dantanarayana | A61M 16/024 128/200.24 |

OTHER PUBLICATIONS

International Search Report for corresponding PCT/EP2021/073687 mailed Nov. 24, 2021, 14 pgs.

International Preliminary Report on Patentability for corresponding PCT/EP2021/073687 mailed Feb. 28, 2023, 7 pgs.

* cited by examiner

VENTILATION DEVICE COMPRISING AN INPUT/OUTPUT DEVICE SECURED TO AN INNER FUNCTIONAL ASSEMBLY

This application claims priority in PCT application PCT/EP2021/073687 filed on Aug. 26, 2021, which claims priority in German Patent Application DE 10 2020 122 672.1 filed on Aug. 31, 2020, which are incorporated by reference herein.

The present invention concerns a ventilation device for at least supportive artificial respiration of patients. The ventilation device comprises:

A device housing,

A functional assembly accommodated in the device housing in an operational position, which exhibits as functional units at least a section of a respiratory gas line, a pressure modification device for modifying a respiratory gas pressure in the respiratory gas line, and a control device for controlling the operation at least of the pressure modification device, and An input/output device arranged at the device housing in an arrangement position, accessible from outside the device housing for its operation, for the input of data and/or control commands into the control device and/or for the output of data and information, where the input/output device is linked with the control device for signal transmission through an aperture in the device housing.

Preferably the ventilation device is an emergency ventilation device as used by emergency physicians and first aiders in emergency situations.

BACKGROUND OF THE INVENTION

As such an emergency ventilator there are known the ventilator with the designation 'EVE$_{IN}$' of Fritz Stephan GmbH in Gackenbach (DE) and the ventilator with the designation 'Falco 202 Evo' of the Italian firm Siare Engineering International Group s. r. l. in Valsamoggia (IT).

Emergency ventilators, inter alia also referred to as 'intensive care ventilators', serve for rapid supply of respiratory gas to a patient outside a clinical environment, i.e. for instance at an accident site and/or during transportation of a patient. Of course, emergency ventilators can also be used in a clinical environment, however in hospitals often more powerful ventilators are available as emergency ventilators.

As ventilators which are deployable outside a clinical environment, emergency ventilators, such as preferably also the present ventilation device, exhibit their own energy store which at least for a certain duration allows operation of the emergency ventilator independently of a power grid supply. Furthermore, emergency ventilators are designed as portable ventilators with regards to their size and weight, such that they can be moved by emergency medical personnel, for instance an emergency physician called to an accident location, with just their own muscle strength even over distances of several dozen meters without excessive physical stress.

Where emergency ventilators exhibit a fan as a preferred pressure modification device, these emergency ventilators can administer at least ambient air as respiratory gas without supplementary special gas reservoirs, such as for instance a detachably coupled oxygen reservoir. To the ambient air there can be added where needed a special gas different from the ambient air, in the most frequent case pure oxygen but also anesthetic and/or therapeutic gases and gas mixtures. To this end, emergency ventilators, such as also that of the present invention, usually exhibit a connector formation for connecting a special gas reservoir.

In order to protect the functional assembly from external influences, such a mechanical impact, dirt and the like, it is arranged in the device housing.

For the input/output device to make possible operation of the ventilation device and the observing of information about an operational state of the ventilation device and/or a respiratory state of a patient who is to be ventilated through the ventilation device, it is arranged at the device housing, namely in such a manner that it is accessible to an operator from outside the device housing. Through the signal-transmitting linking of the input/output device and the control device, signals and consequently data and information can be transmitted between these devices.

SUMMARY OF THE INVENTION

It is the task of the present invention to make possible rapid and secure assembly of the ventilation device.

This task is solved according to the invention in a ventilation device as mentioned at the beginning by having the input/output device secured directly at the functional assembly against removal of the input/output device from its arrangement position in a lifting direction away from the device housing. Consequently, cumbersome mounting both of the input/output device and of the functional assembly on the device housing can be dispensed with. It can then suffice to connect with the device housing only one arrangement consisting of functional assembly and input/output device. The respective other assembly is then held by the one arrangement.

In principle it is conceivable to also secure the input/output device at the device housing against removal in the lifting direction, for instance by engaging from behind an edge of an aperture in the device housing by a formation connected firmly with the input/output device, such as for instance a hook. However, in order to simplify assembly and preferably also disassembly, in a preferred further development of the invention it is provided that the input/output device is secured only at the functional assembly against removal from its arrangement position in the lifting direction away from the device housing.

In principle, the input/output device can penetrate through an aperture of the device housing so that on the one hand the input/output device is accessible from outside for operating the ventilation device and so that on the other hand the input/output device is connected with the control device for signal transmission. Here it is advantageous for the tightest possible sealing of the aperture of the device housing which is penetrated through by the input/output device if the input/output device, under interposition of a section of the device housing between a section of the input/output device and a section of the functional assembly, is secured at the functional assembly against removal from its arrangement position in a lifting direction away from the device housing. Then not only is the input/output device positionally secured at the functional assembly, but over and above that the input/output device and the functional assembly can thus each be fixed relative to the device housing. Moreover, the input/output device can overlap outside the section of the device housing which is interposed between the input/output device and the functional assembly. The interposed section of the device housing, which normally comprises the edge of the aperture of the device housing which is penetrated through by the input/output device, is thus securely covered.

A sealing effect achieved by the input/output device at the interposed section of the device housing can be further increased by having the input/output device clamped at the functional assembly in the direction towards the device housing. Thereby there can in addition be achieved a clamping effect with which the device housing is clamped between the input/output device and the functional assembly. Consequently, the input/output device, the functional assembly, and the device housing as a backlash-free construction unit can be formed just by attaching the input/output device directly to the functional assembly.

According to a first embodiment form, the input/output device can be secured at the functional assembly against removal from its arrangement position in the lifting direction away from the device housing by a fastener configured separately from the input/output device and from the functional assembly, such as for instance at least one screw and/or at least one clip.

For reasons of an advantageously small number of components needed for forming the ventilation device, however, it is preferable that the input/output device is secured at the functional assembly against removal from its arrangement position in the lifting direction away from the device housing by a latching formation configured or arranged at the input/output device and a latching counter-formation configured or arranged at the functional assembly. The two formations: latching formation and latching counter-formation, are then each advantageously provided in a manner which is secure against loss at the arrangements carrying them: input/output device and functional assembly.

In an operational ventilation device, the latching formation is in positive-locking latching engagement with the latching counter-formation, which prevents removal of the input/output device from its arrangement position in the lifting direction away from the device housing. At least one formation out of latching formation and latching counter-formation is here movable at least once from a release position into a latching position along a movement path transversely to the lifting direction. In the release position there exists no positive-locking latching engagement between the latching formation and the latching counter-formation. The then unlatched input/output device is then removable from its arrangement position in the lifting direction away from the device housing. In contrast to this, in the latching position the positive-locking latching engagement is established.

Through the movement of the at least one movable formation out of latching formation and latching counter-formation from the release position into the latching position along the movement path transversely to the lifting direction, the positive-locking latching engagement established in the latching position can support especially high forces in the lifting direction without thereby the positive-locking latching engagement being able to be undone again. Preferably, therefore, the movement path of the at least one movable formation out of latching formation and latching counter-formation is oriented orthogonally to the lifting direction. Since a force acting along the lifting direction has no force component orthogonally to the lifting direction.

In principle, the positive-locking latching engagement between the latching formation and the latching counter-formation can be secured through frictional engagement between an abutment surface of the latching formation and an abutment counter-surface of the latching counter-formation which with an established positive-locking latching engagement abuts against the abutment surface. The frictional engagement can prevent the at least one movable formation moving automatically from the latching position back in the direction of the release position or being moved through forces which arise during operation and in the handling of the ventilation device in the direction of the release position. For a more strongly defined securing of the positive-locking latching engagement, the formation which is movable along the movement path and consisting of the latching formation and the latching counter-formation can be securable in the latching position, against movement out of the latching position, through a securing device, optionally arranged at a distance from the surfaces abutting against each other and consisting of the abutment surface and the abutment counter-surface.

The securing device can be a catch arrangement comprising a catch lug and a catch recess and/or a catch edge. A catch formation consisting of a catch lug on the one hand and a catch recess and/or catch edge on the other can be arranged in a spring-loaded manner in the direction of a catch engagement, such that a catch engagement can arise by itself on reaching a predetermined relative spatial arrangement of catch lug on the one hand and catch recess and/or catch edge on the other. Preferably, therefore, at least one of the catch formations is pre-tensioned in its catch engagement position. In the catch engagement position, the catch lug plunges into the catch recess and/or engages with the catch edge from behind. The catch edge can be an edge which borders the catch recess, such that both the catch recess and the catch edge can be configured at one and the same catch formation.

In principle, the at least one movable formation consisting of latching formation and latching counter-formation can be directly movable by means of manual action from the release position into the latching position, for instance through an engagement aperture in the device housing. To avoid undesirable engagement apertures in the device housing, the ventilation device preferably comprises a drive element through which the movable formation is movable from the release position into the latching position.

The drive element can be a pull and/or push element, which with the movable formation is connected for the transmission of force and movement. The pull and/or push element is preferably connected integrally with the movable formation, for instance as an injection-molded component or as a component otherwise fabricated by molding. For example, the drive element can be a finger or hand grip formation, for instance a finger ring or a tow beam.

For the transmission of high displacement forces along the movement path with at the same time high displacement accuracy, the drive element can comprise a self-locking screw drive. Due to the self-locking configuration of the screw drive, which can be realized through a suitable choice of the thread pitch, the screw drive can be not only the drive element but also the securing device which secures in the latching position the formation which is movable along the movement path and consisting of the latching formation and the latching counter-formation against movement into the release position. Then through a single device, both drive and positional securing of the at least one movable formation can be achieved, which reduces the number of components required for forming the ventilation device.

The screw drive can exhibit a threaded rod and a movement part which is movable relative to the threaded rod through rotation of the threaded rod about the rod's longitudinal axis and which is in screw engagement with the threaded rod. The movement part can be a movable nut, movable gear rod, or movable cog wheel, where the nut, the gear rod, or the cog wheel engages by means of its teeth with the thread of the threaded rod. The threaded rod can, although less preferred, be a hollow threaded rod with an internal thread, through whose rotation a threaded rod with an external thread which is in screw engagement with the hollow threaded rod is displaceable along the common screw axis. Preferably, however, the threaded rod which can be actuated to rotate about the rod's longitudinal axis exhibits an external thread. The movement part is coupled with the at least one formation which is movable along the movement path and consisting of the latching formation and the latching counter-formation for common movement. The threaded rod is normally mounted rotatably about the rod's longitudinal axis on a component of the ventilation device and exhibits with respect to this component only this rotatory degree of freedom.

In principle it can suffice if the formation which is movable along the movement path and consisting of the latching formation and the latching counter-formation is movable only a single time during the manufacturing of the ventilation device from the release position into the latching position. For repeated servicing and where required repair of the ventilation device, however, it is preferable if the formation which is movable along the movement path is movable reversibly between release position and latching position. Then the positive-locking latching engagement can be undone and reestablished.

For clarification let it be noted that the input/output device can arranged latched or unlatched in its arrangement position at the device housing, depending on whether or not the positive-locking latching engagement is established.

The drive element, in particular in its preferred design as a self-locking screw drive, preferably exhibits an actuation formation by means of which a drive force, in particular as a drive torque, can be introduced into the drive element. In the case of a screw drive, this can be a rotatable body through which a torque is introducible into the threaded rod by hand or through tool engagement. For manual action, the actuation formation of a screw drive can be a knurled cylinder, a winghead known from a wing bolt, or generally a rotation-symmetrical body. For tool engagement, the actuation formation of the screw drive can exhibit a known tool engagement formation, such as for instance an external or an internal hexagonal profile, a cross slot, a simple slot, and so forth.

In order to protect the actuation formation, which need only be actuated for assembly and disassembly of the ventilation device, in particular of the input/output device, from unintentional introduction of a drive force, the actuation formation of the drive element can be arranged inside the device housing at least in the release position, preferably both in the release position and in the latching position, of the formation consisting of latching formation and latching counter-formation which is movable by the drive element along the movement path. For the same reason, preferably the whole drive element is arranged inside the device housing at least in the release position, preferably also in the latching position. Moreover, the drive element can thereby be arranged near the at least one movable formation with advantageously short force transmission paths, since with an established positive-locking latching engagement preferably both formations out of the latching formation and latching counter-formation are situated inside the device housing.

So that in the arrangement position the input/output device can completely seal that aperture of the device housing through which it is connected with the control device of the ventilation device for signal transmission, preferably the at least one actuation formation of the drive element, by preference the whole drive element, is accessible for actuation through a different aperture of the device housing than through that aperture through which the input/output device is connected with the control device for signal transmission.

With an advantageously compact structural form the device housing preferably exhibits a prism shape with a housing casing wall at a radial distance from a prism axis encircling the prism axis as a housing component of the device housing. The device housing further exhibits at least one axial, with respect of the prism axis, end-side aperture. Depending on the design of the prism-shaped device housing, it can exhibit just one axial end-side aperture, for instance if the device housing is configured as pot-shaped with a front wall which extends orthogonally to the prism axis at an axial longitudinal end. Or the prism-shaped device housing can exhibit a housing casing wall which is open axially on both sides and then exhibit two axial end-apertures, one each at each axial longitudinal end. This at least one axial end-aperture can in a simple way be closed rapidly and securely by a cover and forms in the unclosed state a relatively large aperture area, which facilitates the assembling of the functional assembly or of individual functional units inside the device housing. At least the actuation formation of the drive element, by preference the whole drive element, is therefore preferably accessible for actuating the drive element through an axial end-side aperture of the at least one axial end-side aperture.

The housing component exhibiting the housing casing wall is preferably a tubular housing component, where its tube axis is the prism axis. For reasons of low weight and good heat conduction, the tubular housing component is preferably formed from a light metal, such as an aluminum or magnesium alloy, can additionally or alternatively also be formed from a copper alloy, such as for example brass or bronze, or also from a copper-containing alloy. In deviation thereof, the tubular housing component can be made from a synthetic, in particular from a thermoplastic synthetic. In order to increase the heat conductance, the synthetic can be filled with particles which increase the heat conductance of the mixture compared with the unfilled synthetic matrix. Such a filling material is for example boron nitride.

For reasons of increased stability, the tubular housing component is preferably fabricated joint-free, for instance as an extruded metal component or as an extruded synthetic component.

Further preferably, the prism-shaped housing exhibits the input/output device in the region of its housing casing wall, by preference only in the region of its housing casing wall.

In an advantageous manner, according to a preferred further development of the present invention the input/output device can be arranged at the device housing backlash-free and even sealing against fluid ingress, if at least one surface, preferably both surfaces, out of an abutment surface of the latching formation and an abutment counter-surface of the latching counter-formation which abuts against the abutment surface when a positive-locking latching engagement is established are inclined to the movement path in such a way that during a movement of the at least one movable formation out of the latching formation and latching counter-formation from the release position into the latching position to establish the positive-locking latching engagement, a force effect is exerted on the input/output device in the direction towards the device housing through a sliding abutment engagement between the abutment surface and the abutment counter-surface. Preferably at least one surface out of the abutment surface and abutment counter-surface, by preference both surfaces, are inclined both to the movement path and to the lifting direction, where the angle of inclination relative to the lifting direction is significantly larger than relative to the movement path, in order to generate through relative movement of the abutment surface and the abutment counter-surface along the movement path a high force between these surfaces parallel to the lifting direction. The aforementioned self-locking screw drive allows the convenient application of the required high displacement forces of abutment surface and abutment counter-surface along the movement path for achieving high clamping forces acting on the input/output device parallel to the lifting direction.

Although it should not be excluded that both the latching formation and the latching counter-formation are arranged along the movement path movably towards and away from one another, it is structurally advantageous and permits a more stable configuration of the latching of the input/output device at the device housing if only one formation out of the latching formation and latching counter-formation is movable between the release position and the latching position. Preferably this is the latching counter-formation, such that then only this one is movable between the release position and the latching position. In the device housing there exists sufficient space for accommodating a latching counter-formation which is movable along the movement path, whereas normally the input/output device is significantly smaller than the device housing and consequently the configuration of a movable latching formation at it is more difficult than at the latching counter-formation. Consequently there is also more installation space available at the functional assembly for accommodating the securing device and/or the drive element than at the input/output device.

According to an advantageous embodiment form, during an assembly of the ventilation device the functional assembly is insertable into its operational position in the device housing through an insertion movement along an insertion path. When using the aforementioned prism-shaped device housing, the insertion path proceeds at least in the region of an end-side axial aperture through which the functional assembly is preferably inserted into the device housing at least tangentially, by preference collinearly to the prism axis. By preference the whole insertion path is parallel or collinear with the prism axis.

The input/output device is displaceable into its arrangement position through an arrangement movement along an arrangement path. The lifting direction normally runs parallel to the arrangement path.

Preferably, one arrangement out of the input/output device and the functional assembly exhibits a plug of a connecting line which transmits signals and/or energy and the respective other arrangement out of the input/output device and the functional assembly exhibits a socket of the connecting line which transmits signals and/or energy, where the plug and the socket are connected with the respective arrangement exhibiting them rigidly and oriented along the insertion path or the arrangement path facing towards one another in such a way that a temporal sequence of an assembly movement consisting of insertion movement and arrangement movement and the respective other assembly movement consisting of insertion movement and arrangement movement effects a fully functional connection of the plug with the socket. Consequently, separately establishing the signal-transmitting connection between the control device and the input/output device can be dispensed with, since this signal-transmitting connection is established automatically with the positioning of the functional assembly in the device housing and with the positioning of the input/output device in its arrangement position.

The input/output device preferably comprises at least one display device, such as for instance a monitor, in order to output therewith data and information perceivably for an operator. The display device preferably comprises a touchscreen, such that it can also serve for the input of data and information. Additionally or alternatively, the display device can exhibit illuminants which can be either lit up or not lit up and output information as a function of their state of illumination.

Additionally or alternatively, the input/output device can exhibit at least one switch, such as for instance at least one pushbutton and/or at least one rotary switch, as input means for the input of data and information. To facilitate both the assembly and the operation of the ventilation device, preferably all input means such as for instance switches, touchscreen etc of the ventilation device are arranged at the input/output device. Alternatively or preferably additionally, all output means such as monitor, illuminants, loudspeakers etc of the ventilation device are arranged at the input/output device.

The functional assembly can in principle be formed from several separate functional units. To facilitate assembling, the functional assembly comprises a preassembled module consisting of at least the section of a respiratory gas line, the pressure modification device, and the control device, which as a preassembled module is insertable into the device housing and/or is withdrawable from the latter. The preassembled module can comprise further functional units, such as for instance an active or passive cooling device for the dissipation of heat from the pressure modification device and/or accommodation of an energy store and/or the energy store itself. The functional assembly as a preassembled module can additionally be complemented by individual separate functional units which are not part of the preassembled module.

Because of the facilitated assembly of the ventilation device, the functional assembly preferably comprises all functional units of the ventilation device as a preassembled module, with the exception of the input/output device. A further exception can be an electrical energy store, which can be accommodated exchangeably in an accommodating space, for instance a duct. In this case, the functional assembly as part of the preassembled module can preferably exhibit the accommodating space for accommodating an electrical energy store. The electrical energy store, for instance a battery or a rechargeable storage battery, can even be accommodated detachably in the accommodating space during the assembly of the ventilation device. Alternatively, a preassembled electrical energy store can be installed in the functional assembly. Then the energy store can also be part of the preassembled module of the functional assembly.

A filter for the cleaning of respiratory gas can likewise be part of the functional assembly. Since with continued operation of the ventilation device the filter normally becomes dirty and loses cleaning performance and/or volume throughput capacity, it is preferably provided as replaceable at the functional assembly. The preassembled module preferably comprises an accommodated volume for detachable accommodation of a filter, in particular a filter cartridge. A filter cartridge is a vessel through which gas flows with a filter body accommodated inside it in the flow path from the gas inlet to the gas outlet of the vessel. The filter can thus be handled without having to touch the filter body as the carrier of the filtering and cleaning function.

An advantage, if the functional assembly exhibits all functional units of the ventilation device as preassembled, lies in the simple servicing of the functional units. These can, as a preassembled module after undoing the positive-locking latching engagement with few hand movements, especially preferably in a single work step, be exposed and made accessible by pulling out of the device housing, in particular out of the prism-shaped or tubular housing component. As further functional units the functional assembly can exhibit a power supply unit, at least one mixing valve for mixing of air and at least one special gas, a cooling device for dissipating heat from the vicinity of the fan, the aforementioned drive element and the aforementioned securing device, and the like. The cooling device can be an active cooling device, such as for instance a cooling fan, but for reducing the energy consumption of the ventilation device is preferably a passive cooling device, such as for instance a heat-conducting body made from a good heat-conducting material such as metal, in particular aluminum or copper or alloys containing these metals. For improving the heat transfer from the cooling device to the device housing, a heat-transfer surface of the passive cooling device can be clamped with a clamping device against an abutment surface of the device housing provided for this purpose. The clamping device can comprise one or several screws.

The device housing, in particular the prism-shaped or tubular housing component, is preferably a purely passive component and forms a shell around the functional assembly and also a support for the input/output device.

All the operationally required connectors such as sockets, gas line couplings, electrical connecting lines, gas inlet apertures, and gas outlet apertures are preferably also provided ready for use at the functional assembly. Then especially advantageously a final inspection of the functional units for their correct functioning can be performed before the final assembly of the ventilation device, which considerably reduces the outlay on defect rectification.

The pressure modification device preferably comprises a fan. It can additionally or alternatively comprise at least one valve. The fan and/or the valve are controllable through the control device in their operation, i.e. at least are switchable on and off. Preferably the fan can be varied in its operating performance through the control device. Likewise preferably the at least one valve can be actuated through the control device with stepped or continuously variable aperture cross-section.

The input/output device is preferably secured through the positive-locking latching engagement directly to the functional assembly, where normally a section of the device housing is situated between a section of the functional assembly on the one hand and a section of the input/output device on the other, such that the input/output device can be clamped with force against the device housing through the positive-locking latching engagement with the functional assembly. This configuration not only requires a small number of components in total, but also prevents incorrect assembly and a disassembly made necessary thereby with reassembly. Because the input/output device can only be latched at the device housing in the arrangement position when the functional assembly is situated correctly in its operational position in which establishing the positive-locking latching engagement is possible.

Preferably the positive-locking latching engagement secures not only the input/output device against removal from the device housing in the lifting direction, but also secures the functional assembly against removal from the device housing along the insertion path in a direction opposite to the insertion movement.

It should not be excluded here that the functional assembly reaches its operational position only through establishment of the positive-locking latching engagement. In any case, in the advantageous design being discussed here of the ventilation device the positive-locking latching engagement can only be established effectively when the functional assembly is situated in its operational position and the input/output device in its arrangement position.

For the case that the device housing exhibits a prism shape with a housing casing wall encircling a prism axis at a radial distance from the prism axis and with at least one axial end-side aperture with respect to the prism axis, the functional assembly as a component of the preassembled module preferably exhibits a cover, which with a functional assembly introduced completely into the operational position covers an axial end-side aperture of the at least one axial end-side aperture of the device housing. The cover preferably exhibits at least one operationally required connector, by preference a plurality of operationally required connectors, such as for example sockets and/or gas line couplings and/or electrical connecting lines and/or a gas inlet aperture and/or a gas outlet aperture.

Consequently, until the arrangement of the functional assembly in its operational position there is available an axial end-side aperture as an assembling aperture, which during the arrangement of the functional assembly in the operational position is readily closed by means of the cover of the preassembled functional assembly. The cover consequently serves also for visual inspection of the arrangement of the functional assembly in its operational position inside the device housing through observation of the device housing from outside.

If the device housing exhibits the aforementioned prism-shaped or tubular housing casing wall which is open at both sides at the longitudinal end and in addition to the cover of the preassembled module of the functional assembly a second cover as a housing component, where the second cover can be mounted separately from the functional assembly onto the housing casing wall as a housing component of the device housing for closing one of the longitudinal ends and preferably can be removed again, this second cover preferably exhibits access passages penetrating through it through which at least one operationally required connector, such as a socket and/or a gas line coupling and/or an electrical connecting line and/or—especially preferably—a gas inlet aperture and/or a gas outlet aperture is accessible.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which forms a part hereof and wherein.

DESCRIPTION OF PREFERRED EMBODIMENTS

Figure 1:
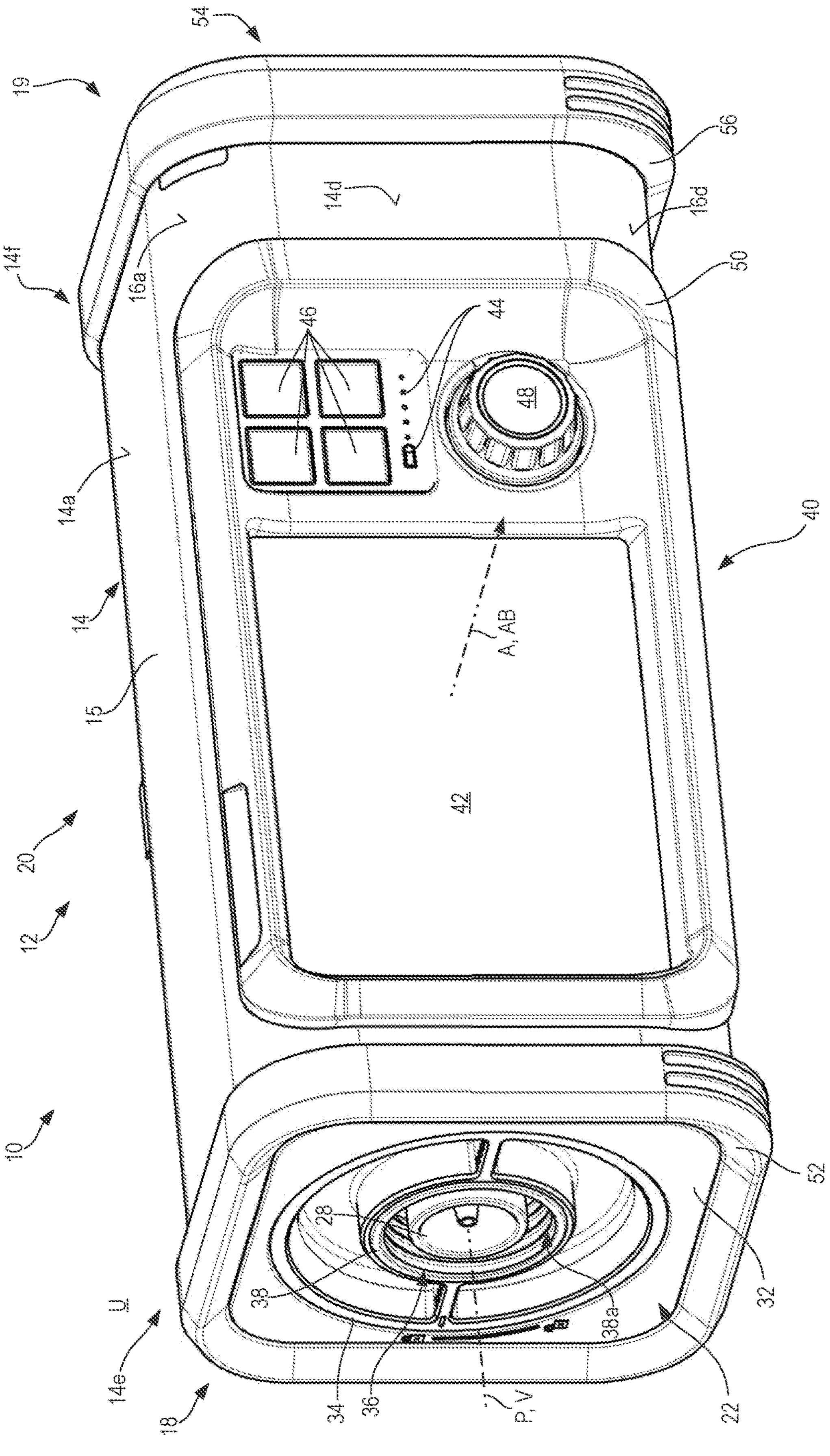
FIG. 1 A perspective view of a ventilation device according to the invention in a preferred embodiment as emergency ventilator, FIG. 2 A perspective exploded view of a prism-shaped housing component and of the functional assembly of the emergency ventilator according to the invention of FIG. 1, FIG. 3 A perspective exploded view of the functional assembly and of the input/output device of the emergency ventilator according to the invention of FIG. 1, FIG. 4 The functional assembly and the input/output device of FIG. 3 with established positive-locking latching engagement, and FIG. 5 A plan view of the front face of the emergency ventilator of FIG. 1 facing away from the observer in FIG. 1.

Referring now to the drawings wherein the showings are for the purpose of illustrating preferred and alternative embodiments of the invention only and not for the purpose of limiting the same, in FIG. 1, an embodiment form according to the invention of a ventilation device according to the invention in a preferred embodiment as an emergency ventilator is labelled generally by 10. The emergency ventilator 10 comprises a device housing 12 with a prismatic basic form, in the present case with a cuboidal basic form with rounded edges.

Figure 2:
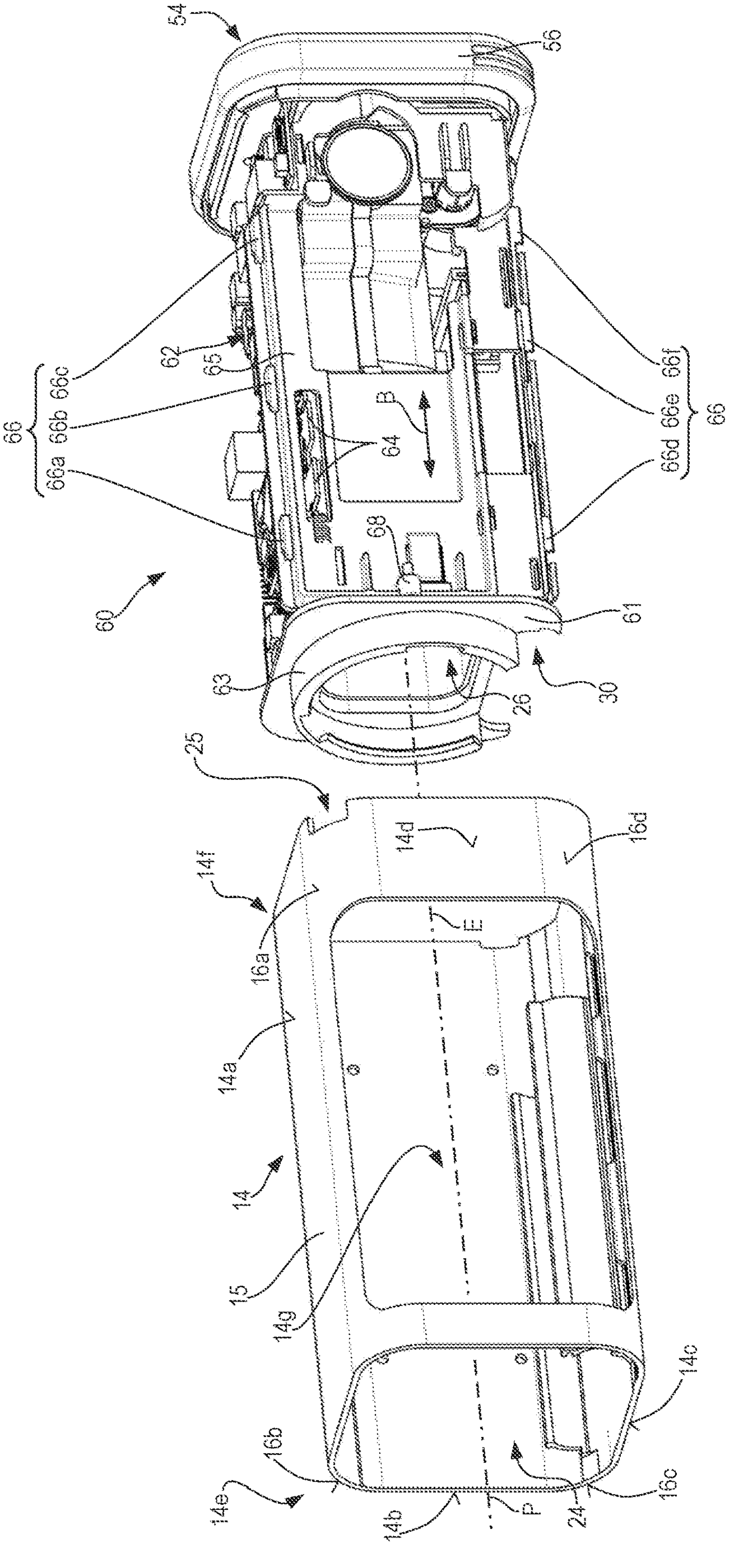

The housing casing wall 14 of the device housing 12 comprises four planar surface segments 14*a*, 14*b*, 14*c*, and 14*d* (only the top and the front planar surface segments 14*a* and 14*d* respectively can be seen in FIG. 1, for the rest see FIG. 2), of which planar surface segments 14*a*, 14*b*, 14*c*, and 14*d* following one another respectively in the circumferential direction about the prism axis P are oriented orthogonally to one another. All planar surface segments 14*a*, 14*b*, 14*c*, and 14*d* are parallel to the prism axis P. The planar surface segments 14*a*, 14*b*, 14*c*, and 14*d* are connected with one another, preferably joint-free, through curved, preferably quarter-cylindrical, surface segments 16*a*, 16*b*, 16*c*, and 16*d* (only the top front and the bottom front curved surface segments 16*a* and 16*d* respectively can be seen in FIG. 1, for the rest see FIG. 2). The individual cylinder axes of the quarter-cylindrical and thereby curved surface segments 16*a*, 16*b*, 16*c*, and 16*d* are parallel to the prism axis P. The housing casing wall 14 is preferably formed by an extruded aluminum tube 15 as a component of the device housing 12.

On the front face 18 of the housing 12 facing towards the observer of FIG. 1 the device housing 12 comprises a housing cover 22 which is removable from the rest of the device housing 20 along the prism axis P and arrangeable at the rest of the device housing 20. The housing cover 22 consequently serves to close a housing aperture 24 (see FIG. 2) which is configured at the longitudinal end 14*e* of the housing casing wall 14 lying nearer to the observer of FIG. 1. The housing aperture 24 is bordered by the housing casing wall 14 of the rest of the housing 20. Through the housing aperture 24 when the cover 22 is removed there is accessible a filter accommodating compartment 26 (s. FIG. 2) for an air filter cartridge 28 with an air filter and there is accessible a storage battery accommodating compartment 30 (s. FIG. 2) for a rechargeable electric storage battery as a power grid-independent energy store.

The housing cover 22 exhibits a cover component 32 and a closure component 34. The closure component 34 is mounted on the cover component 32 rotatably about the closure axis V. The closure axis V proceeds in the closed state, i.e. when the housing cover 22 is arranged at the rest of the housing 20 and closes the housing aperture 24, coaxially with the prism axis P.

The housing cover 22 exhibits besides an ambient air aspiration aperture 36 which penetrates through both the cover component 32 and the closure component 34. Through the ambient air aspiration aperture 36 there can be aspirated by a fan as a pressure modification device ambient air from the environment U through the air filter cartridge 28 into a fan space in the housing 12.

The closure component 34 is shown in FIG. 1 in its closed position, from which it is rotatable counterclockwise by about a twelfth of a rotation about the closure axis V into an open position indicated by a symbol in the shape of an open padlock.

The ambient air aspiration aperture 36 is bordered immediately radially outward—with respect to the latching axis V—by a mounting section 38 of the cover component 32. The mounting section 38 exhibits an attachment formation 38*a* in the form of an internal thread. At this attachment formation 38*a* there can for example be arranged an additional air filter which performs filter functions that the air filter of the air filter cartridge 28 does not carry out. Alternatively or additionally there can be arranged at the attachment formation 38*a* a measuring device which captures metrologically the ambient air flowing through the ambient air aspiration aperture 36, for instance determines its chemical composition or determines whether and if applicable to what extent the aspirated ambient air does or does not contain a predetermined component.

On the planar surface segment 14*d* and starting from it extending into the part-cylindrical surface segments 16*d* and 16*a* adjacent in the circumferential direction about the prism axis P, the emergency ventilator 10 exhibits an input/output device 40 arranged in an arrangement position which serves for information exchange between an operator and the emergency ventilator 10 and which serves for controlling the emergency ventilator 10 by the operator. The input/output device 40 exhibits a monitor 42 as an output device, which preferably is a touchscreen which permits in a touch-sensitive manner the input of information. The input/output device 40 exhibits furthermore display LEDs 44 as a further output device for example for depicting the charging state of the electric storage battery of the emergency ventilator 10 and exhibits for example a pushbutton switch 46 and a rotary switch 48 as input means.

For protection from external stresses and for sealing against the housing casing wall 14, the input/output device 40 is surrounded by a synthetic material frame 50, for instance made from a thermoplastic synthetic. In the frame 50 there can be accommodated an elastomer seal completely extending all around the circumference together with the frame 50, which abuts in a sealing manner both against the frame 50, there preferably in an accommodating groove, and against the housing casing wall 14.

The instrument cover 22 is surrounded by a shock-absorbing elastomer ring 52 completely encircling the prism axis P in the circumferential direction. In the closed state the elastomer ring 52 covers a part of the housing casing wall 14 in like manner to the front face 18, such that in the region of the instrument cover 22 the elastomer ring 52 protects the emergency ventilator 10 both against axial and against radial impact stresses.

At the longitudinal end 14*f* of the housing casing wall 14 opposite the instrument cover 22 there is likewise arranged an instrument cover 54. In contrast to the instrument cover 22, the instrument cover 54 is preferably not removable on its own from the housing casing wall 14 of the housing 12. In order to also protect the longitudinal end of the instrument cover 54 from axial and radial impact stresses, there is also provided at this longitudinal end an elastomer ring 56 encircling the prism axis P in a completely closed manner in the circumferential direction, which covers both a part of the housing casing wall 14 and a part of the front face 19. The front face 19 is opposite the front face 18 with respect to the prism axis P.

In the unlatched state, the input/output device 40 is removable from the device housing 12 along an arrangement path AB in a lifting direction A out of the arrangement position shown in FIG. 1.

In FIG. 2, the prism-shaped aluminum tube 15 as component of the device housing 12 and a functional assembly 60 which in the operational state is arranged inside the device housing 12 are depicted in an exploded view.

The housing casing wall 14 exhibits on its side which faces towards the observer of FIG. 2 a large aperture 14*g* through which a control device 62 of the functional assembly 60 can be connected with the input/output device 40 for signal transmission.

The functional assembly 60 can be inserted into the aluminum tube 15 as part of the device housing 12 along an insertion path E which is collinear with the prism axis P, through an axially end-side aperture 25 in the longitudinal end 14*f* of the housing casing wall 14 and accordingly of the aluminum tube 15.

The functional assembly 60 comprises the control device 62 already mentioned above on its side facing upwards in FIG. 2. On combustion safety grounds, the control device 62 is arranged constructionally separated in the functional assembly 60 from respiratory gas lines conducting inspiratory respiratory gas, including pure oxygen as an optional special gas. In an atmosphere with an elevated oxygen content compared with normal air, the heating up of electric and electronic components of the control device 62 or a spark forming undesirably can have a combustive effect, which is why the pressure modification device in the form of a fan which is likewise contained preassembled in the functional assembly 60 and the respiratory gas lines in which the respiratory gas conveyed by the pressure modification device flows are constructionally strictly separated from the control device 62. The pressure modification device and the respiratory gas lines are therefore no discernible in FIG. 2. In the depicted preferred embodiment example, the cover 54 is likewise part of the functional assembly 60 preassembled as a module, which can be inserted as a module into the aluminum tube 15 in a single assembly step along the insertion path E. An engagement formation 63 which protrudes along the insertion path E from an end plate 61 of the functional assembly 60 serves for arranging the cover 22, in particular the closure component 34 at the rest of the device housing 20 when the functional assembly 60 is in its operational position inside the device housing 12.

Two edge connectors 64 project out of the control device 62 in parallel to the arrangement path AB. They serve to make a signal-transmission connection directly between the control device 62 and the input/output device 40 solely by arranging the functional assembly 60 in its operational position and by arranging the input/output device 40 in its arrangement position.

Facing towards the observer of FIG. 2, there is situated at the functional assembly 60 movable back and forth along a movement path B in parallel to the insertion path E and accordingly to the prism axis P a carrier 65 with a latching counter-formation 66, which in FIG. 2 is in its release position in which it is arranged nearer to the cover 54. The latching counter-formation 66 comprises in the depicted example six latching wedges 66*a*, 66*b*, 66*c*, 66*d*, 66*e*, and 66*f*, of which three are arranged on the upper side and three on the lower side. All latching wedges together form the latching counter-formation 66. The carrier 65 is movable along the movement path B relative to the end plate 61 and to the rest of the immovable functional units of the functional assembly.

Figure 3:
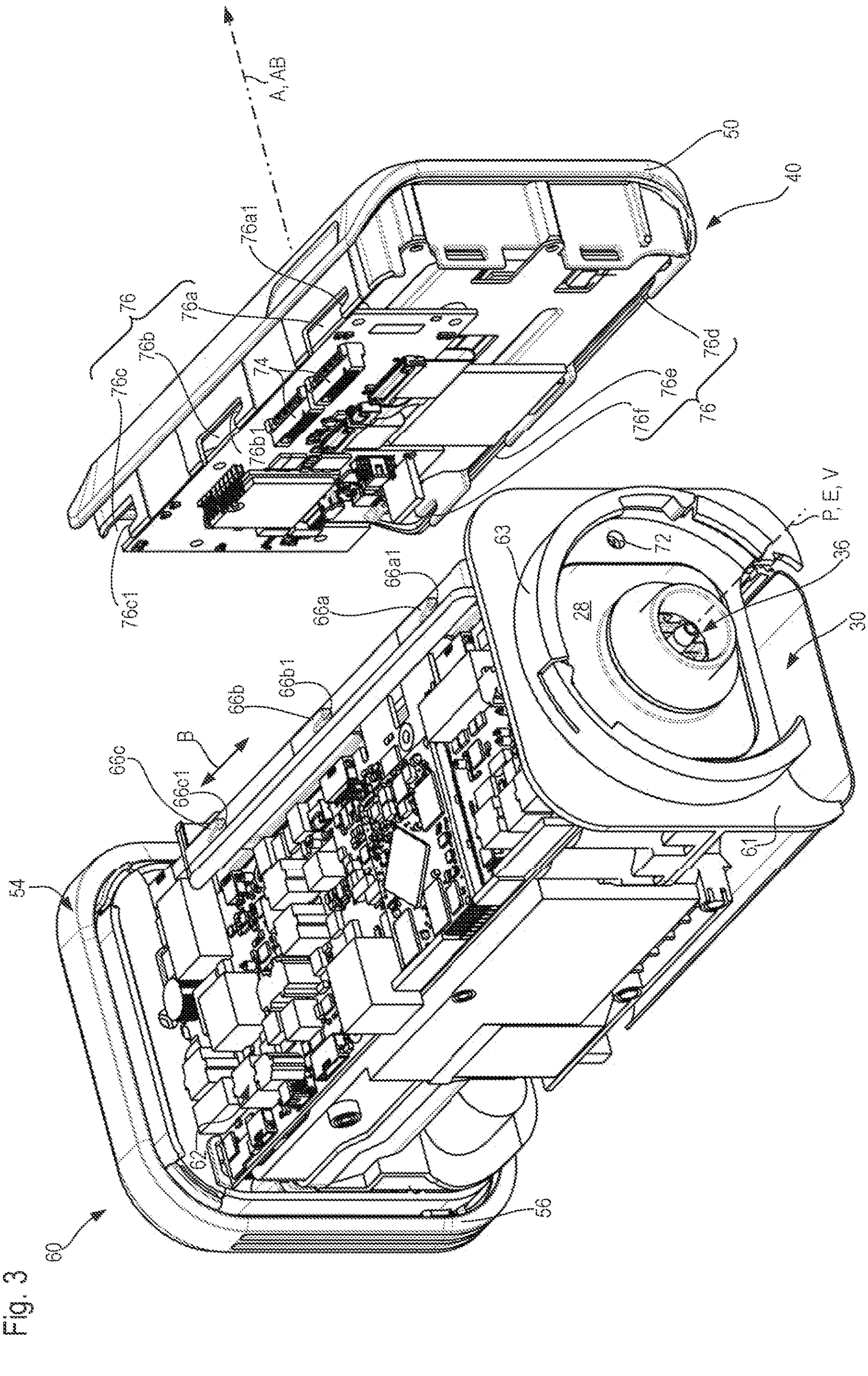

The carrier 65, which for example is configured as a synthetic injection-molded component, is displaceable along the movement path B by means of a screw drive 68. In FIG. 3 the actuation formation 72 with cross-slot tool engagement formation of a screw and/or threaded rod as the case may be of the screw drive 68 is depicted to the right of the filter accommodating compartment 26. Since the screw drive 68 is self-locking, a movement of the carrier 65 can only be effected via the actuation formation 72, but no movement of the actuation formation 72 through movement of the carrier 65. Therefore the screw drive 68 also acts as a securing device for securing the position of the carrier 65 and thereby of the latching counter-formation 66 in the respective position reached by actuating the actuation formation 72.

In FIG. 3, the input/output device 40 is depicted obliquely from above and behind, such that of the input/output device 40 mainly its back is discernible. The input/output device 40 comprises electronic components for operating the monitor 42, the further display device 44, and the switches 46 and 48. The input/output device 40 further comprises at its back two connecting sockets 74 sticking out in parallel to the arrangement path AB, against the lifting direction, into which the edge connectors 64 are inserted when the functional assembly 60 is in its operational position and the input/output device 40 approaches the housing casing wall 14 against the lifting direction A.

The input/output device 40 shows besides, preferably configured integrally at its frame 50, a latching formation 76 which is configured as complementary to the latching counter-formation 66 of the functional assembly 60. The latching formation 76 exhibits in total six engagement recesses 76*a*, 76*b*, 76*c*, 76*d*, 76*e*, and 76*f*, in which the latching wedges 66*a*, 66*b*, 66*c*, 66*d*, 66*e*, and 66*f* engage for establishing a positive-locking latching engagement. In contrast to the latching counter-formation 66, the latching formation 76 is not movable relative to the device carrying it, here: input/output device 40, but rather is arranged rigidly at the frame 50 of the input/output device 40.

When the functional assembly 60 is in its operational position and the latching counter-formation 66 is in its release position, the input/output device 40 can be brought into its arrangement position against the lifting direction A, where the latching wedges 66*a*, 66*b*, 66*c*, 66*d*, 66*e*, and 66*f* already engage with the engagement recesses 76*a*, 76*b*, 76*c*, 76*d*, 76*e*, and 76*f* but as yet without establishing a positive-locking latching engagement which prevents lifting of the input/output device 40 in the lifting direction A. This is effected only through movement of the latching counter-formation 66 along the movement path B in the direction away from the cover 54 into the latching position.

Using the example of the engagement recess 76*a* there is shown in FIG. 3 an abutment surface 76*a*1, which with an established positive-locking latching engagement is in abutment against an abutment counter-surface 66*a*1 of the latching wedge 66*a*. Every engagement recess 76*a*, 76*b*, 76*c*, 76*d*, 76*e*, and 76*f* exhibits an abutment surface each, where the abutment surfaces are preferably identical. For the sake of better clarity, in FIG. 3 only the upper abutment surfaces 76*a*1, 76*b*1, and 76*c*1 are labelled with reference numbers. Likewise, every latching wedge 66*a*, 66*b*, 66*c*, 66*d*, 66*e*, and 66*f* exhibits one abutment counter-surface each, where the abutment counter-surfaces are preferably identical. Once again for the sake of better clarity, only the upper abutment counter-surfaces 66*a*1, 66*b*1, and 66*c*1 are labelled with reference numbers.

The abutment surfaces and abutment counter-surfaces are slightly inclined relative to the movement path B, such that they are slightly inclined relative to the lifting direction A from a reference plane orthogonal to the lifting direction A. The inclination is such that during a displacement of the latching counter-formation 66 along the movement path from the release position into the latching position, a force acting opposite the lifting direction is exerted by the inclined abutment counter-surfaces on the abutment surfaces and thereby on the input/output device 40. Consequently by establishing the positive-locking latching engagement, the input/output device 40 can be clamped by the latching counter-formation 66 towards the housing casing wall 14.

Figure 4:
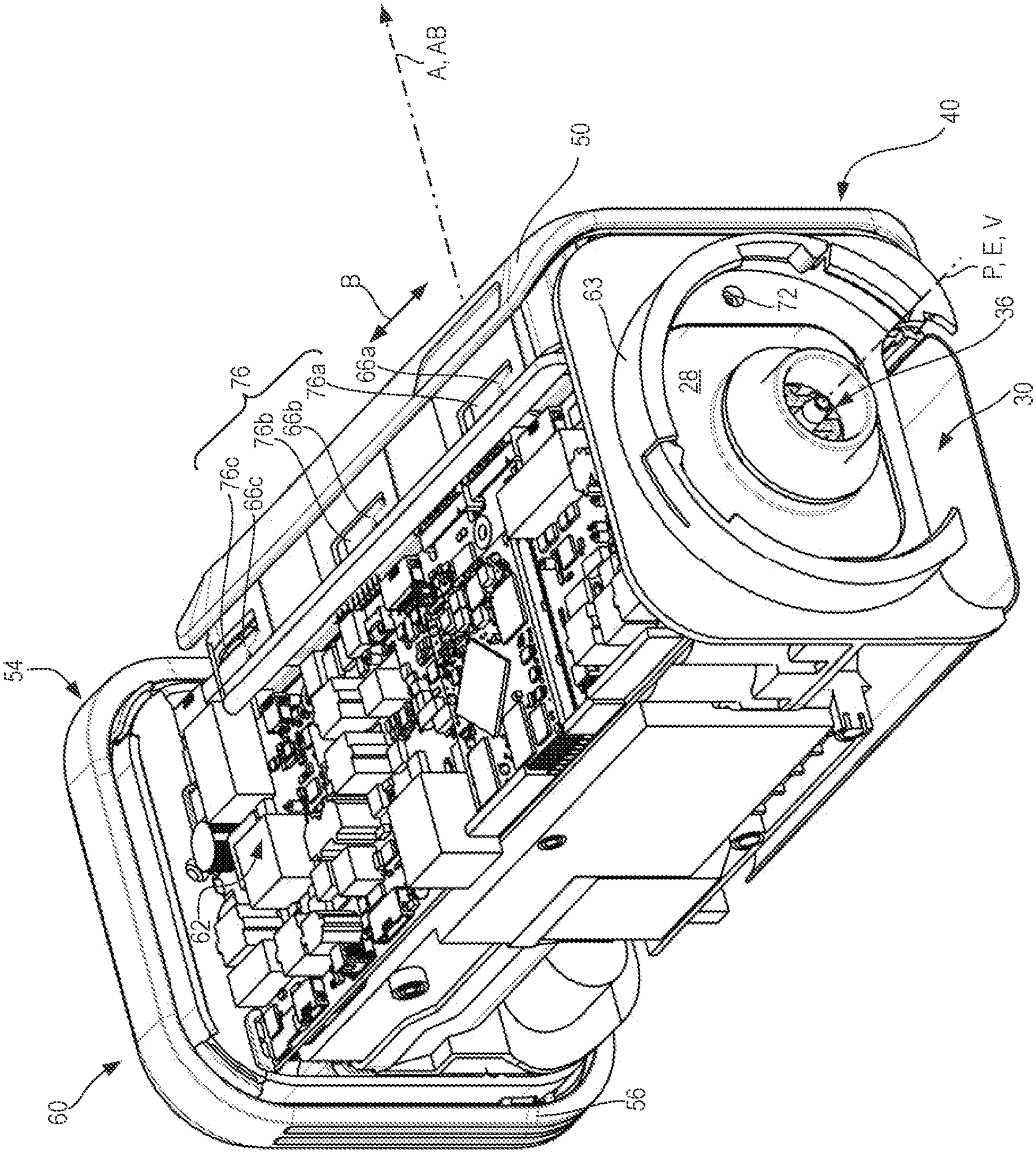

In FIG. 4 the functional assembly 60 and the input/output device 40 are shown in the same perspective as in FIG. 3, where the input/output device 40 is in its arrangement position and the latching counter-formation 66 has been brought into its latching position. Consequently, the input/output device 40 is on the one hand connected with the control device 62 for signal transmission through insertion of the edge connectors 64 into the sockets 74 and on the other through establishment of the positive-locking latching engagement between the latching formation 76 and the latching counter-formation 66 secured against removal in the lifting direction A from the functional assembly 60 and from the housing casing wall 14 which is not depicted in FIG. 4. The screw drive 68 holds with its self-locking effect the latching counter-formation 66 in the latching position shown in FIG. 4.

Figure 5:
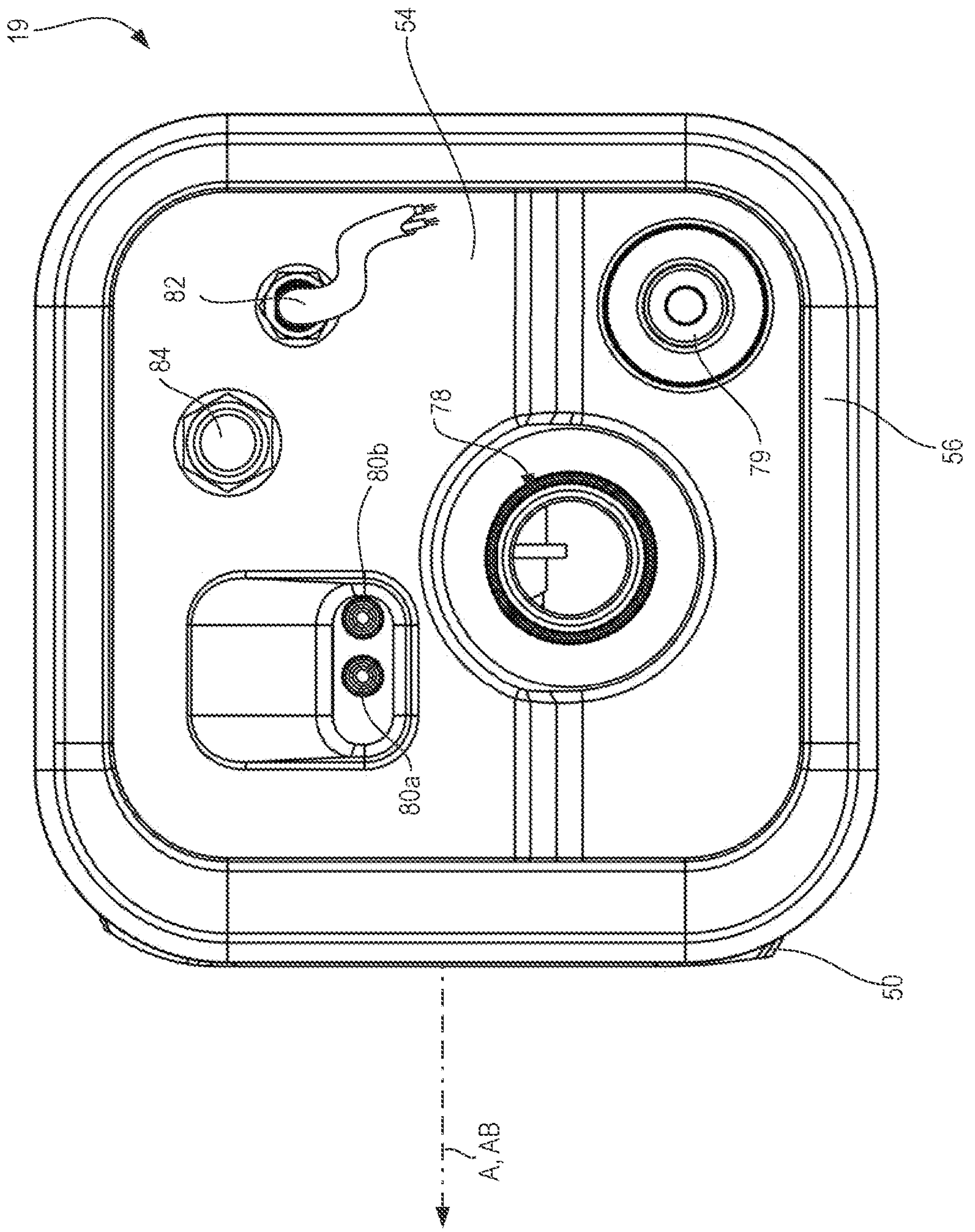

Solely for the sake of completeness, in FIG. 5 there is depicted a view of the front face 19 of the emergency ventilator 10. FIG. 5 shows a respiratory gas output aperture 78, through which inspiratory respiratory gas conveyed by the fan of the pressure modification device exits from the device housing 12 towards a patient connected to the emergency ventilator 10. The respiratory gas output aperture 78 forms an end of a respiratory gas line of the functional assembly 60. At a special gas coupling section 79 there can be introduced into the respiratory gas line a supply device for supplying as an inspiratory respiratory gas or a component of same a gas which differs from the air as respiratory gas aspirated by the fan.

FIG. 5 further shows connection nozzles 80*a* and 80*b* to which pressure acquisition hoses are connectable which at their other end lying distally from the connection nozzles 80*a* or 80*b* respectively are each connected with an inner region of a differential pressure flow sensor for measuring a proximal inspiratory and preferably also expiratory respiratory gas flow. The two inner regions of the differential pressure flow sensor are separated from one another in a manner known per se through a flow resistance which is variable through the respiratory gas flow.

Given spatial availability of a power connection, the emergency ventilator 10 can be operated via a power input 82 with energy from an external power supply grid such as for instance from a public power supply grid or from the on-board supply grid of a vehicle or aircraft. All electrical functional units of the emergency ventilator 10 can then be supplied with grid energy, where the grid voltage is transformed to DC low voltage via a power supply unit as a further functional unit of the preassembled functional assembly 60. Likewise, the not depicted storage battery can be recharged. A socket 84 in the housing 12 is arranged for connecting an external sensor, in particular $CO_2$ sensor. Such a $CO_2$ sensor can for example be provided at a flow sensor coupled with the emergency ventilation device 10 and be coupled to a sensor arrangement.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. A ventilation device for at least supportive artificial respiration of patients, comprising:

a device housing, a functional assembly accommodated in the device housing in an operational position, which exhibits as functional units at least a section of a respiratory gas line, a pressure modification device for modifying a respiratory gas pressure in the respiratory gas line, and a control device for controlling the operation at least of the pressure modification device as functional units of the functional arrangement accommodated in the device housing, and an input/output device arranged at the device housing in an arrangement position, accessible from outside the device housing for its operation, for the input of data and/or control commands into the control device and/or for the output of data and information, where the input/output device is linked with the control device for signal transmission through an aperture in the device housing, where the input/output device is removably secured directly and only to the functional assembly against removal of the input/output device from its arrangement position in a lifting direction away from the device housing, where the input/output device is secured only to the functional assembly against removal from its arrangement position in the lifting direction away from the device housing.

2. The ventilation device according to claim 1, wherein a portion of the housing is between the input/output device and the functional assembly when the input/output device is secured to the functional assembly against removal of the input/output device from its arrangement position in a lifting direction away from the device housing.

3. The ventilation device according to claim 2, wherein the input/output device on the functional assembly is urged in the direction towards the device housing.

4. The ventilation device according to claim 1, wherein the input/output device is secured at the functional assembly against removal from its arrangement position in the lifting direction away from the device housing by a fastener configured separately from the input/output device and from the functional assembly.

5. The ventilation device according to claim 1, wherein the input/output device is secured at the functional assembly against removal from its arrangement position in the lifting direction away from the device housing by a latching formation configured or arranged at the input/output device and a latching counter-formation configured or arranged at the functional assembly.

6. The ventilation device according to claim 5, wherein in a ready-to-operate ventilation device, the latching formation and the latching counter-formation are in positive-locking latching engagement with one another, where at least one formation out of latching formation and latching counter-formation is movable at least once from a release position into a latching position along a movement path transversely to the lifting direction, where in the release position there exists no positive-locking latching engagement between the latching formation and the latching counter-formation and the then unlatched input/output device is removable from its arrangement position in the lifting direction away from the device housing, and where in the latching position the positive-locking latching engagement is established.

7. The ventilation device according to claim 6, wherein only the latching counter-formation is movable between the release position and the latching position.

8. The ventilation device according to claim 1, wherein the device housing exhibits a prism shape with a housing casing wall at a radial distance from a prism axis encircling the prism axis and with at least one axial, with respect of the prism axis, end-side aperture.

9. The ventilation device according to claim 8, wherein the input/output device is secured at the functional assembly against removal from its arrangement position in the lifting direction away from the device housing by a latching formation configured or arranged at the input/output device and a latching counter-formation configured or arranged at the functional assembly; and only the latching counter-formation is movable between the release position and the latching position.

10. The ventilation device according to claim 1, wherein a portion of the housing is between the input/output device and the functional assembly when the input/output device is secured to the functional assembly against removal of the input/output device from its arrangement position in a lifting direction away from the device housing; wherein in a ready-to-operate ventilation device, a latching formation and a latching counter-formation are in positive-locking latching engagement with one another, where at least one formation out of latching formation and latching counter-formation is movable at least once from a release position into a latching position along a movement path transversely to the lifting direction, where in the release position there exists no positive-locking latching engagement between the latching formation and the latching counter-formation and the then unlatched input/output device is removable from its arrangement position in the lifting direction away from the device housing, and where in the latching position the positive-locking latching engagement is established; and wherein at least one surface out of an abutment surface of the latching formation and an abutment counter-surface of the latching counter-formation which abuts against the abutment surface when a positive-locking latching engagement is established are inclined to the movement path in such a way that during a movement of the at least one movable formation out of the latching formation and latching counter-formation from the release position into the latching position to establish the positive-locking latching engagement, a force effect is exerted on the input/output device in the direction towards the device housing through a sliding abutment engagement between the abutment surface and the abutment counter-surface.

11. The ventilation device according to claim 10, wherein both surfaces out of the abutment surface of the latching formation and the abutment counter-surface of the latching counter-formation which abuts against the abutment surface when the positive-locking latching engagement is established are inclined to the movement path in such a way that during the movement of the at least one movable formation out of the latching formation and latching counter-formation from the release position into the latching position to establish the positive-locking latching engagement, the force effect is exerted on the input/output device in the direction towards the device housing through the sliding abutment engagement between the abutment surface and the abutment counter-surface.

12. The ventilation device according to claim 10, wherein the input/output device is secured at the functional assembly against removal from its arrangement position in the lifting direction away from the device housing by a latching formation configured or arranged at the input/output device and a latching counter-formation configured or arranged at the functional assembly; and only the latching counter-formation is movable between the release position and the latching position.

13. The ventilation device according to claim 1, wherein during assembling of the ventilation device the functional assembly is insertable into its operational position in the device housing by means of an insertion movement along an insertion path and the input/output device is displaceable into its arrangement position by means of an arrangement movement along an arrangement path, where one arrangement out of the input/output device and the functional assembly exhibits a plug of a connecting line which transmits signals and/or energy and the respective other arrangement out of the input/output device and the functional assembly exhibits a socket of the connecting line which transmits signals and/or energy, where the plug and the socket are connected with the respective arrangement exhibiting them rigidly and oriented along the insertion path or the arrangement path facing towards one another in such a way that a temporal sequence of an assembly movement out of insertion movement and arrangement movement and the respective other assembly movement out of insertion movement and arrangement movement effects a fully functional connection of the plug with the socket.

14. The ventilation device according to claim 1, wherein the functional assembly is a preassembled module consisting of at least the section of a respiratory gas line, the pressure modification device, and the control device, which as a preassembled module is insertable into the device housing and/or is withdrawable from the latter.

* * * * *